United States Patent [19]
Ishikawa et al.

[11] Patent Number: 4,830,494
[45] Date of Patent: May 16, 1989

[54] METHOD AND APPARATUS FOR MEASURING PARTICLES IN A FLUID

[75] Inventors: Muneharu Ishikawa, Tama; Kouichi Akiyama, Hino; Eiichi Ito, Toyohashi; Masunori Kawamura; Akihiro Fujita, both of Hino, all of Japan

[73] Assignee: Kowa Company Ltd., Aichi, Japan

[21] Appl. No.: 72,228

[22] Filed: Jul. 9, 1987

[30] Foreign Application Priority Data

Jul. 10, 1986 [JP] Japan .................. 61-160829
Jul. 10, 1986 [JP] Japan .................. 61-160830
Jul. 10, 1986 [JP] Japan .................. 61-160831
Jul. 18, 1986 [JP] Japan .................. 61-167788
Jul. 23, 1986 [JP] Japan .................. 61-171863

[51] Int. Cl.$^4$ ............................................. G01N 21/47
[52] U.S. Cl. .................................. 356/336; 250/574; 356/339
[58] Field of Search ............ 356/336, 339, 246; 250/564, 574, 576

[56] References Cited

U.S. PATENT DOCUMENTS 4,226,532 10/1980 Berber et al. .................. 356/339 X
4,265,538 5/1981 Wertheimer .................. 356/336 X
4,521,521 6/1985 Abbott et al. .................. 356/336 X Primary Examiner—Davis L. Willis
Assistant Examiner—Matthew W. Koren
Attorney, Agent, or Firm—Bruce L. Adams; Van C. Wilks

[57] ABSTRACT

Disclosed is a method and apparatus for measuring particles in a fluid by irradiating the fluid containing the particle with a laser beam and analyzing the laser light scattered by the particle to determine the characteristics of the particle. An elliptical laser beam is projected into a particle detection area in which the particles to be measured are caused to flow. The laser light scattered by the particle is received for photoelectric conversion into a time-series photoelectric signal in a direction along which the particle flows. The photoelectric signal is subjected to a moving average process to determine a time width during which the signal exceeds a predetermined level to cause the change in intensity of the scattered light. This change is recognized as a change in intensity caused by the passage of the particle through the particle detection area when the time width falls within a certain range.

29 Claims, 15 Drawing Sheets

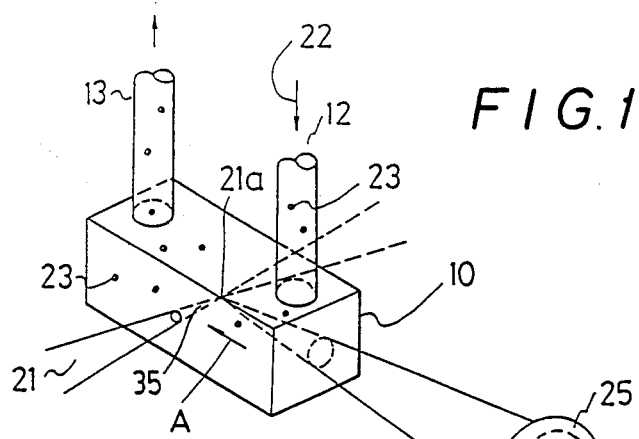
FIG. 1
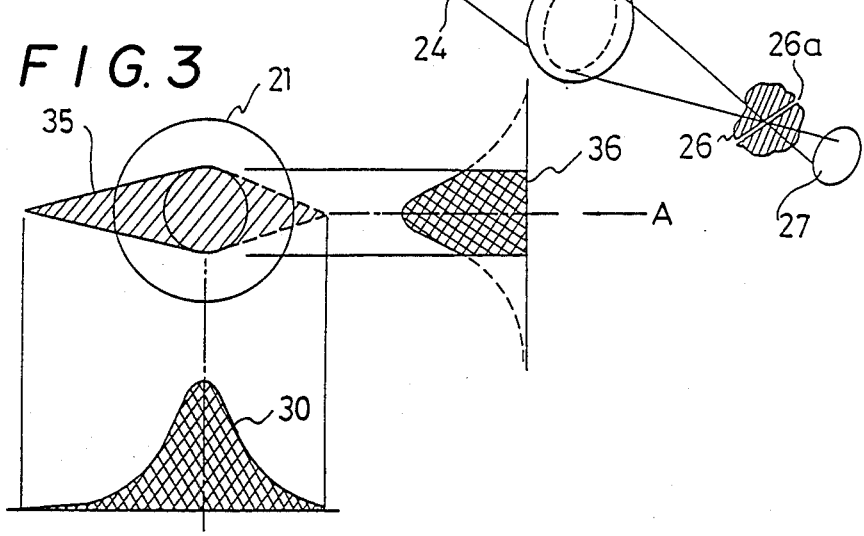
FIG. 3
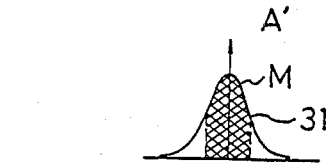
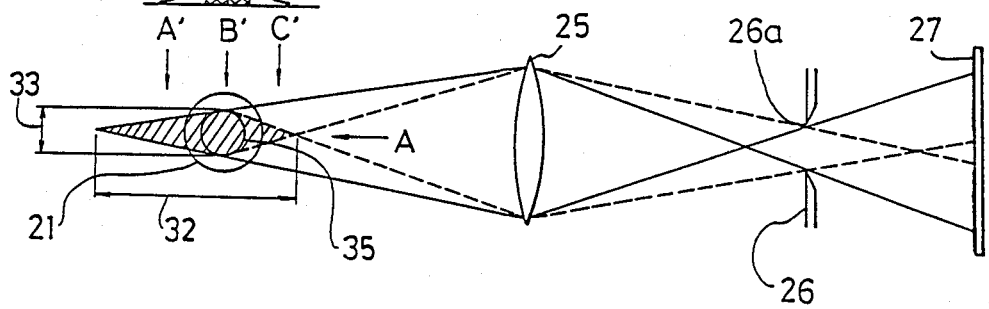
FIG. 2

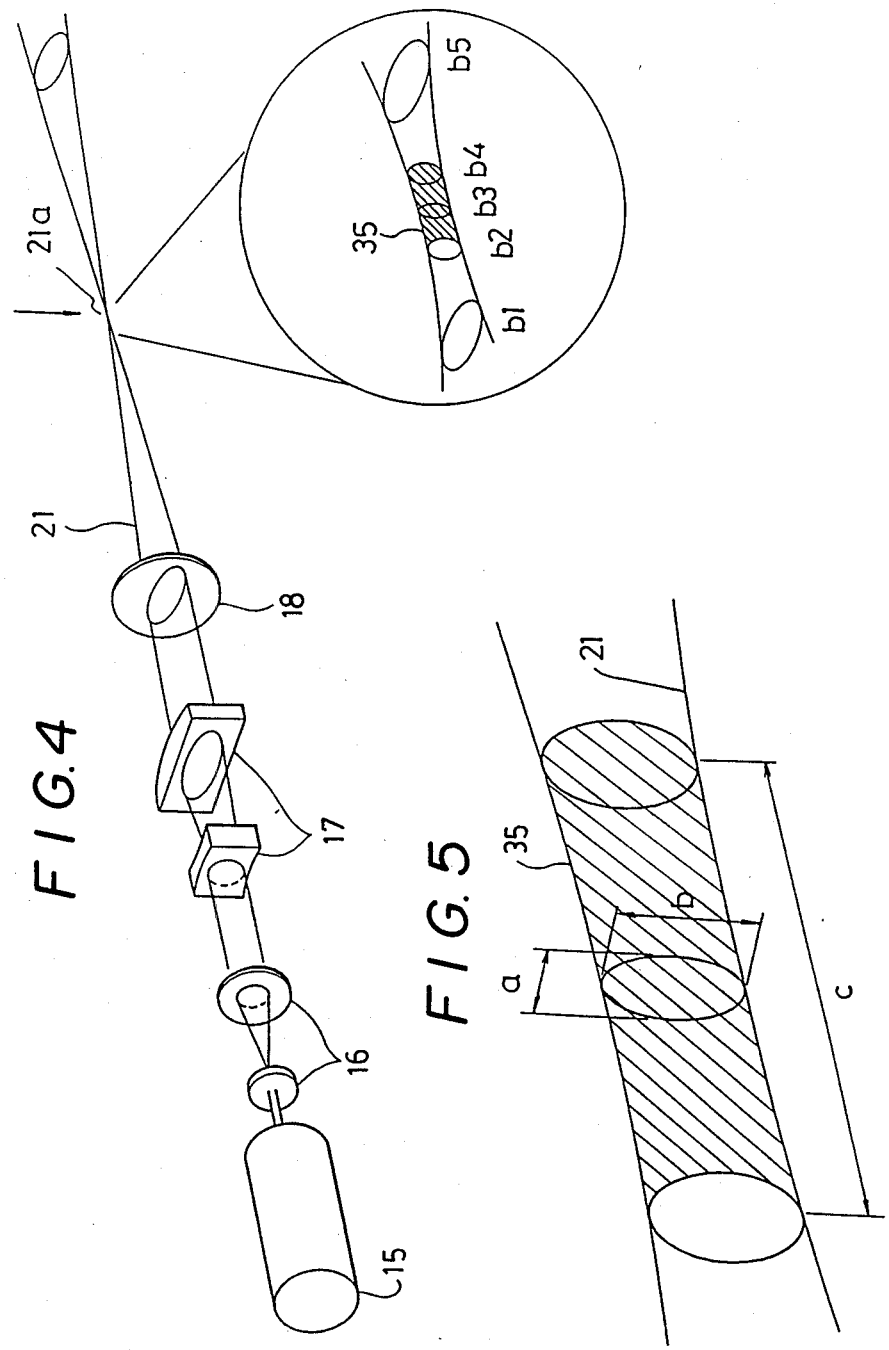

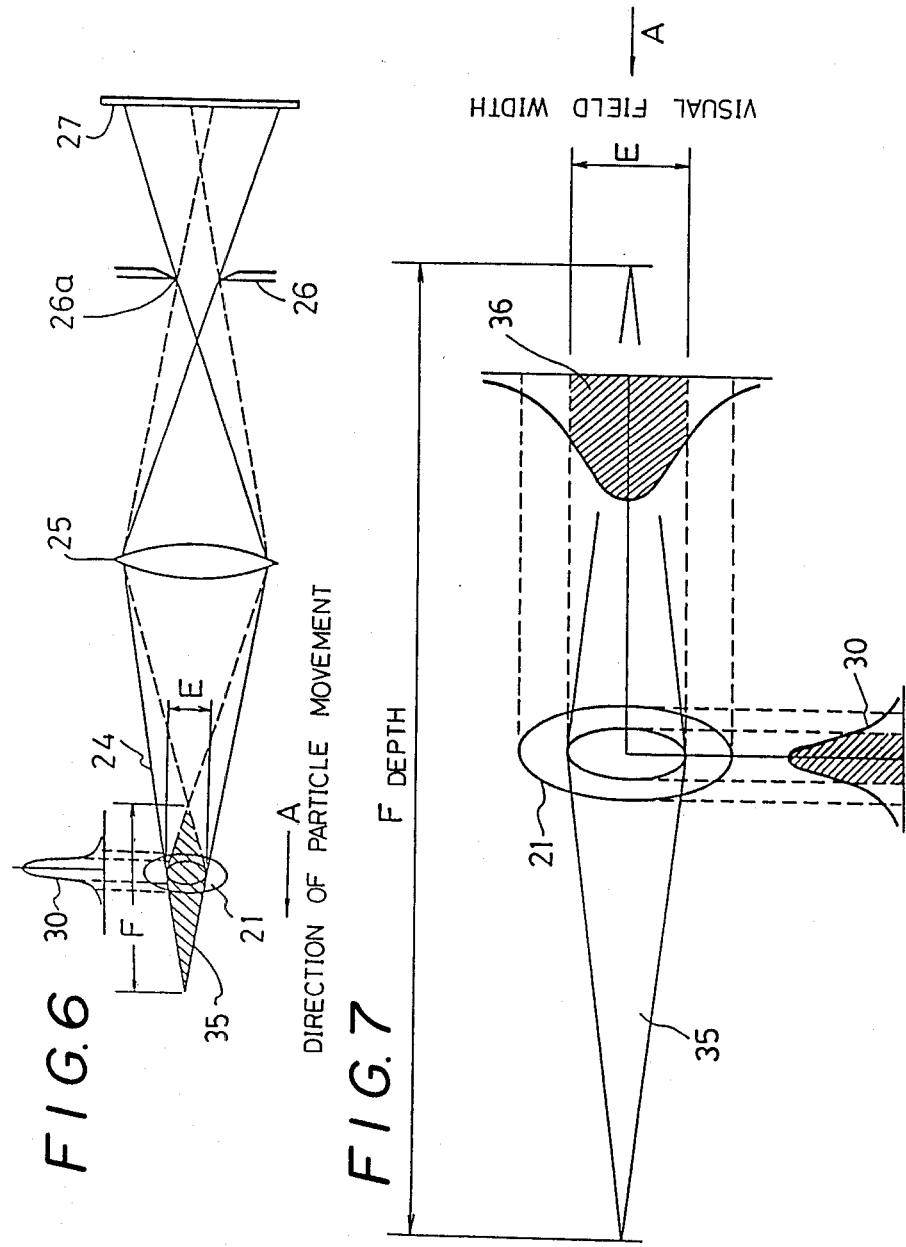

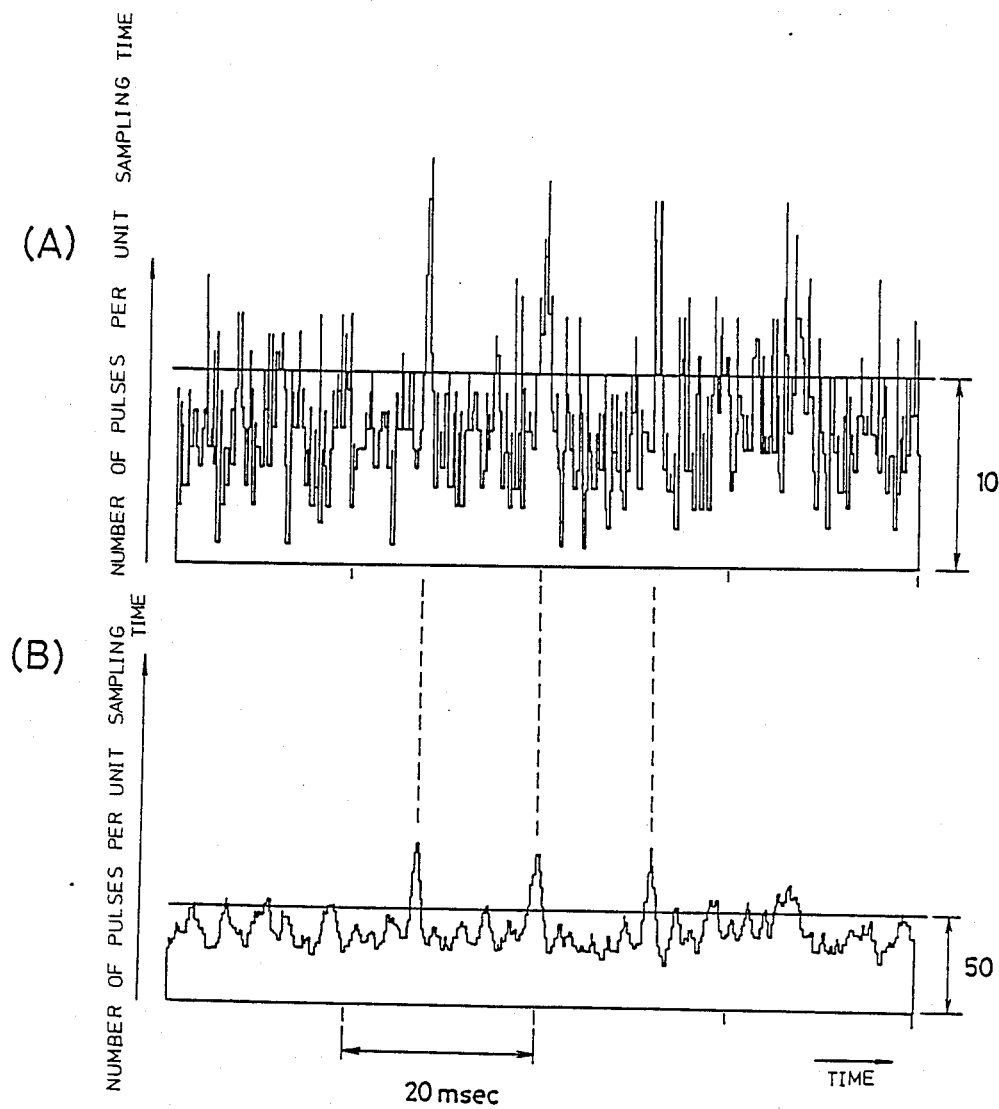

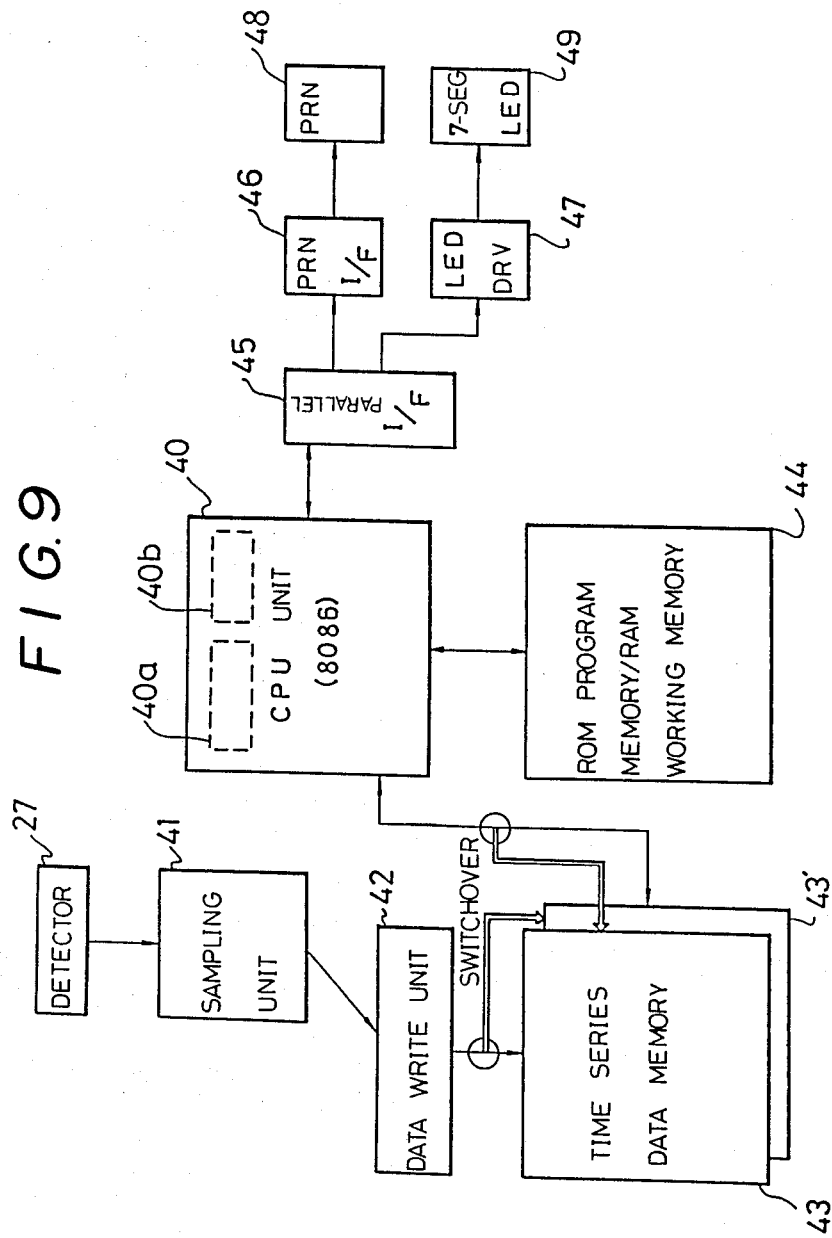

METHOD AND APPARATUS FOR MEASURING PARTICLES IN A FLUID

BACKGROUND OF THE INVENTION

1. Field of the Invention

This invention relates to a method and apparatus for measuring fine particles in a fluid, and more particularly to a method and apparatus for measuring particle characteristics such as diameter and the number of the particles by irradiating a flowing fluid with laser light and detecting the laser light that is scattered by the particles in the fluid.

2. Description of the Prior Art

A conventional method for determining particle characteristics such as the diameter and number of particles is to irradiate a measuring area with light and measure the amount of light that is transmitted, the scattering characteristics and the like.

This method is for example used to determine particulate impurities contained in purified water. However, because of the small size of the particles in the water and their sparse distribution, such measurement is difficult. Because of this, there has been employed a method whereby a high-luminance measuring area is formed by concentrating a beam of irradiating light from a laser light source or the like into a small area in order to increase the intensity of the scattered light from the particles, and receiving the light scattered by particles that pass through this area.

In a particle measuring apparatus in which particles are irradiated with laser light and the light scattered by the particles is analyzed, how the measuring portion through which the particles are caused to pass is formed is important. In the case of particles in a gas, the gas containing the particles is blown out from a nozzle and surrounded by purified gas to form the measuring area. In the case of the measurement of particles in a fluid, a measuring cell is required which maintains the fluid and causes the fluid to flow.

Because of the irradiation by the laser light, the surfaces of the measuring cell through which the laser light beam enters and exits, and the surface which receives the scattered light, need to be optically transparent. A four-sided translucent cell is used when the scattered light is received in a direction perpendicular to the direction in which the laser beam is projected, and a two-sided translucent cell is used when the scattered light is received in the forward direction of the laser beam.

With such a method, in most cases the spot of converged laser light is used as the particle detection area formed in the measuring cell to increase the scattering intensity. Also, with this system the fluid containing the particles is measured just one time when the fluid is passed through the cell, because the fluid is discharged after the measurement.

In particular, various techniques for measuring the particles are used, because the cross-sectional shape of the laser beam that forms the particle detection area, the direction of the passage of the particles and the method of setting the mask optimally are directly dependent on the capability of resolving the particle diameter of the system in which the particle diameter is determined from the intensity of the light scattered by the particles.

Previously, because the particles to be measured were relatively large, that is, up to 0.2 micrometers, the intensity of the light scattered by the particles was high, and even when particles in pure water were to be measured, there was no need to increase the concentration of the laser beam in order to distinguish the light scattered by the particles from background light by water. Therefore, there was no need to reduce the size of the mask which sets the effective diameter of the light beam constituting the particle detection area to full width at half maximum.

However, for background-light recognition and detection of particles measuring 0.1 micrometers or less, it was necessary to tightly focus the laser light forming the particle detection area into a beam having a diameter on the order of 10 micrometers and limit the length of the detection area in the direction of the optical axis to about the same, so as to thereby control the intensity of the background light. In order to realize this, a mask having a slit on the order of 10 micrometers is disposed at the imaging position of the receiving lens which collects the scattered light. However, even if the mechanical precision of the system is increased, it is not easy to constantly maintain a mask having this small slit at the optimum position in an environment subject to vibration and fluctuations in temperature. Especially for the round-the-clock on-line measuring systems, it is possible that the scattered-light imaging position on the mask surface will be moved as a result of variations in the day-to-day ambient atmospheric temperature, distortion caused by heat given off by heat sources such as the internal laser light source, and vibration.

Also, with a particle-measuring apparatus based on the light-scattering method, in order to distinguish light scattered by particles from the light scattered by the fluid at the particle detection area (hereinafter referred to as "background light"), a particle recognition system is used wherein the scattered-light intensity is converted into electrical signals, a few threshold values for the signal are set, every series of signals exceeding the threshold values is recognized as particles, and the number of particles classified according to the threshold values are counted as the particle distribution.

However, when the particle size is around 0.1 micrometers, the light scattered by the particles is weak, so that in order to extract the particle-scattered light the volume of the particle detection area has to be reduced to weaken the background light, which gives rise to a large fluctuation in the electrical signals, and it becomes difficult to clearly distinguish the signal pulses corresponding to the weak particle-scattered light from the fluctuation component, using the said particle recognition method. The cause of this lies in the use of only the signal pulse amplitude for particle recognition.

SUMMARY OF THE INVENTION

An object of this invention is therefore to provide a method and apparatus for measuring particles in a fluid whereby the intensity of scattered light from a particle does not greatly vary according to the position of the particle passage, so that low-error, accurate particle measurement is possible.

Another object of this invention is to provide a method and apparatus for measuring particles in a fluid whereby the particle acquisition ratio can be increased without reducing the intensity of the laser beam, in addition to which the diameter of the laser beam in the direction of the particle passage through the area is shortened, enabling changes in the intensity of the scattered light due to the passage of the particles to be made more abrupt and conspicuous.

A further object of this invention is to provide a method and apparatus for measuring particles in a fluid whereby a laser beam focussing system is used to enable fine particles to be detected, while the sample fluid is measured several times, thereby enabling particle detection efficiency to be raised.

A still further object of this invention is to provide a method and apparatus for measuring particles in a fluid whereby stable measurement of scattered light can be carried out even in the presence of external disturbing factors such as temperature variations and vibration.

A still another object of this invention is to provide a method and apparatus for measuring particles in a fluid which enables particles to be reliably recognized on the basis of the intensity of the scattered light from particles passing through the particle detection area.

According to the present invention, a particle detection area is formed in a measuring cell in which the particle to be measured is caused to flow. The laser beam is projected into the particle detection area, and the laser light scattered by the particle is received in a direction along which the particle flows and then analyzed to determine the characteristics of the particle.

With this arrangement, it is possible to effectively utilize the characteristics of an optical system whereby the width of the visual field is limited by selecting another direction of the particle's passage, enabling the same effect to be obtained as when the particle has passed through only the effective beam area. That is, because changes in the intensity of scattered light from the same particles are limited to corresponding changes in the intensity distribution of the laser beam, within the effective beam area, it is possible to obtain the scattered light of about the same intensity from any one particle of the same diameter irrespective of the particle passage position in the particle detection area, thereby increasing the resolving power of the particle diameter calculated from the intensity of the scattered light.

In a preferred embodiment, an elliptical laser beam is used so as to form a laser beam having its elliptical section at the particle detection area.

With this arrangement, it is possible to increase the particle image acquisition ratio by increasing the sectional area of the particle detection area perpendicular to the direction of the particle's passage while maintaining the intensity of the laser beam, thereby establishing a detection area suitable for the detection of fine particles.

Further, in the present invention, the fluid flowing into the measuring cell in the form of a jet is mixed with the fluid within the measuring cell to form a turbulent flow. The thus formed mixture is then stirred into a whirling stream and is led to the particle detection area.

The measuring cell thus formed solves the contradiction of a conventional cell between the flow rate and the particle detection efficiency. That is, the fluid is steadily fed into the cell at high rate of flow and the particles are brought to the detection area by the whirling stream and turbulent mixing flow. Furthermore, the representative particles providing the characteristics of the particle size distribution of the whole fluid can be detected. Thus the detection efficiency of particles in the sample fluid can be effectively increased.

In the present invention, a photoelectric detector is used to receive the laser light scattered by the particle in the direction along which the particle passes. Preferably, a mask having a slit is disposed in the front of the photoelectric detector for limiting the scattered laser beam impinging thereon. The mask is successively driven until it reaches a position in which the intensity of background light is at a maximum.

With this arrangement, the mask on the imaging plane of the light receiving lens which limits the particle detection area formed at the spot at which the laser light is converged is controlled automatically to enable the mask to be adjusted to acquire the full width at half maximum of the laser light at the detection area. The position of the mask in the scattered-light receiving system can thus be automatically set constantly to the optimum position.

Further in the present invention, the laser light scattered by the particle is photoelectrically converted into a time-series electric signal, which is processed to determine a time width during which a change in intensity of the scattered laser light occurs in which the time-series electric signal exceeds a predetermined level. The change in intensity of the scattered light is recognized as a change in intensity caused by the passage of the particle through the particle detection area when the time width falls within a certain range. After recognition, data derived from the photoelectrical detector are further processed to determine the characteristics of the particle.

In the present invention thus constructed, two conditions are selected for recognizing that a signal pulse obtained from the particle-scattered light is a signal arising from a particle. The first is that the signal exceeds a predetermined value that has been set to exclude virtually all the background light from the particle recognition process; and the second, which applies to the signals that exceed the predetermined value, is that the time-width of the signal change arising from a change in the intensity of the scattered light produced when a particle passes through the particle detection area is within a certain set range. When the time-width of the signal value during which a change in the scattered-light intensity is produced that is above the predetermined value is obtained, and this time-width value is within the set range, it is recognized as a change in intensity due to the passage of a particle, enabling the particle measurement precision to be increased. Measurement can be performed with a high particle-diameter resolution, especially when individual particle recognition is being carried out, and when the distribution of particle size and numbers is obtained by converting the maximum measured values into sizes using only the measured value data of what have been recognized as particles.

BRIEF DESCRIPTION OF THE DRAWINGS

The objects and features of the present invention will become more apparent from a consideration of the following detailed description taken in conjunction with the accompanying drawings in which:

FIG. 1 is an explanatory view illustrating the principle of the method of this invention;

FIG. 2 is an explanatory view showing the effect of providing a mask on the light receiving side;

FIG. 3 is an explanatory view showing the relationship between the direction of flow of the particles and the distribution of the scattered light;

FIG. 4 is an abridged view of the construction of an elliptical laser beam forming apparatus;

FIG. 5 is an enlarged view of the particle detection area when an elliptical laser beam is used;

FIG. 6 is an explanatory view illustrating an example configuration for the particle detection area when an elliptical laser beam is used;

FIG. 7 is an explanatory view of the relationship between the depth in the particle detection area and the visual field;

FIG. 8A is a waveform of the sampled pulses obtained from the photoelectric detector, and FIG. 8B is a pulse waveform that has been subjected to moving average processing;

FIG. 9 is a block diagram of the particle recognizing apparatus;

DETAILED DESCRIPTION OF THE PREFERRED EMBODIMENTS

Figure 10:
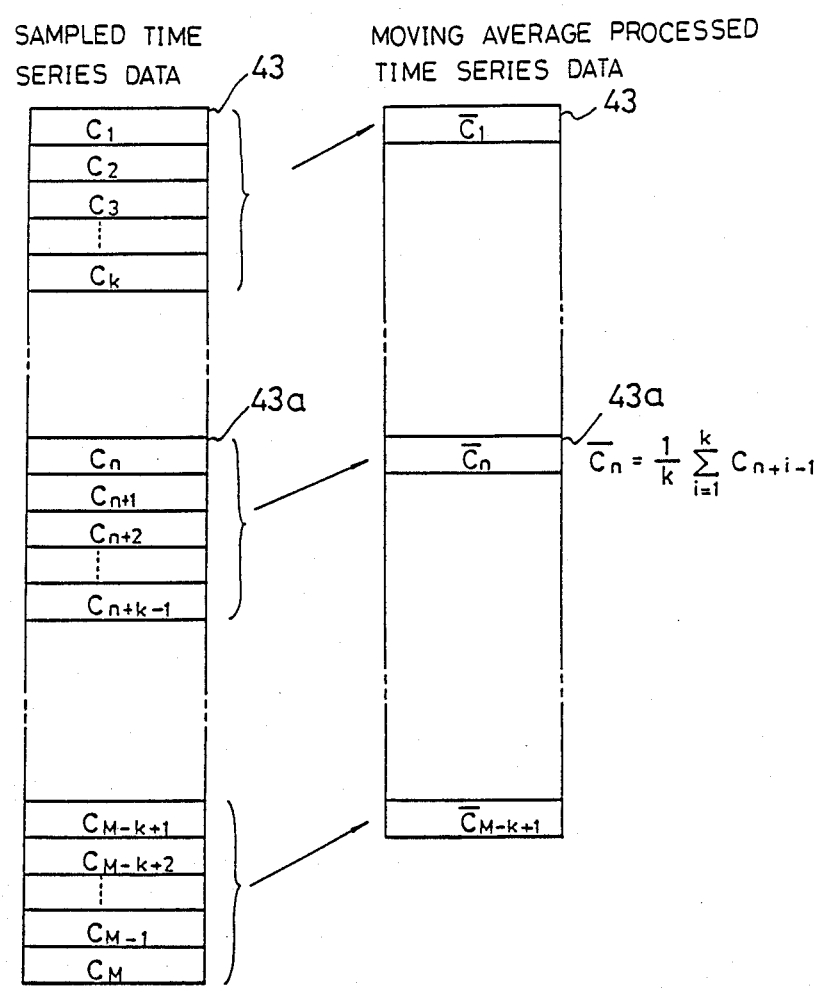
FIG. 10 is an explanatory view illustrating moving average processing of time-series data.

This invention will now be described in detail on the basis of the preferred embodiments illustrated in the accompanying drawings.

With reference to FIG. 1 showing the principle of the particle measuring apparatus of this invention, a laser beam 21 passes through a converging lens and is concentrated into a light spot 21a in a square block shaped measuring cell 10. The vicinity of the light spot 21a forms a particle detection area 35. A sample fluid 22 such as pure water or the like which contains fine particles 23 which are to be detected is supplied through a fluid intake pipe 12, passed through the particle detection area 35 and expelled from a fluid discharge pipe 13. Scattered light 24 from particles on which the laser beam 21 impinges passes through a light receiving lens 25 to a mask 26 for detection by an photoelectric detector 27, and particle recognition is performed as explained later.

As shown in FIG. 2, usually the intensity of the laser beam 21 has a distribution M that is Gaussian in a plane perpendicular to the optical axis. As a result, the intensity of the scattered light from a particle passing through the beam changes according to the position of the particle along its passage, so that the intensities of the scattered light from particles (A',B', C') differ from each other even when the particles have the same diameter. As shown in the drawings, a method of limiting the particle detection area is used which consists of disposing the mask 26 having a slit 26a on an imaging plane which is conjugate with the light beam with respect to the scattered light receiving lens 25.

Here, the particle detection area indicated in the drawing by the shaded portion is defined by the F-number, the focal length, the magnifying power of the light receiving lens 25 and the slit width. When the F-number becomes small, the depth 32 of the detection area becomes shallow, but it is difficult for it to become more shallow than the visual field width 33 set by the slit width and the magnifying power. Thus it is difficult to limit the particle detection area 35 to only the effective beam area 31 shown by the cross-hatched portion (meaning non-detection of particles A' and C').

Thus, as long as the incident laser beam 21 has a Gaussian intensity distribution, the relationship between the aforementioned visual field width 33 and depth 32 cannot be improved, and all particles that pass the positions A', B', C' indicated in FIG. 2 will be detected.

In the present invention, the scattered light 24 from the particles 23 passing through the particle detection area 35 formed by the laser beam 21 is received in the direction A of the particle's passage and the particle characteristics are determined therefrom.

FIG. 3 illustrates the relationship at issue between the particle detection area 35 and the direction of a particle's passage. The laser beam 21 is shown as double circles. The outer of these double circles shows the position at which the intensity of the beam becomes $1/e^2$ the center intensity; usually, the diameter of this outer circle is referred to as the beam diameter. The inner circle shows the position at which the intensity of the beam becomes $\frac{1}{2}$ the center intensity; the diameter of the inner circle is termed the full width at half maximum of the beam. The shaded portion in the drawing is the particle detection area 35 defined by the mask selected to limit the particle detection area to the beam's full width at half maximum, the cross-hatched portions 30 and 36 represent the maximum intensity distribution of the light received when a particle passes through the laser beam 21 in the said particle detection area. When the direction of the particle passage is A', the intensity distribution is elongated into a bell shape, but with the A direction system proposed by the present invention, the intensity distribution coincides with the said effective beam area and in the limited particle detection area 35 the proper intensity distribution can be obtained.

In the present invention a configuration is used wherein the direction of the particle's passage through the particle detection area 35 is perpendicular to the light axis and the particle-scattered light is received in the direction A.

With the thus formed measuring cell, the area of the light spot 21a becomes the detection area 35 shown in FIG. 1, and the intensity distribution of the laser light becomes as shown by the cross-hatched portion 36, approximately coinciding with the effective beam area. With the beam having this intensity distribution, the scattered light 24 from the fine particles is imaged at the mask 26 by the receiving lens 25, and the scattered light limited by the slit 26a reaches the photoelectric detector 27 and is measured.

This invention uses an elliptical laser beam to form a more effective particle detection area. The apparatus to produce the elliptical laser beam is shown in FIG. 4. Laser light from a laser light source 15 is expanded by a beam expander 16, passes through cylindrical lenses 17 which convert the beam into the elliptic form, and is converged into the light spot 21a via the lens 18. The vicinity of the light spot 21a forms the detection area 35. The laser beam is flattened horizontally at b1 and b5 fore and aft of the detection area 35, while at b2, b3 and b4 of the area, the beam is flattened vertically.

The shape of this particle detection area is characterized by three lengths a, b and c as shown in FIG. 5. Here, a and b indicate the diameters of the elliptical beam 21 at the light spot, and c indicates the length along the beam axis. If I is the beam intensity, Wb is the amount of scattered light from the sample fluid in the effective particle detection area and W is the amount of scattered light from passing particles, then $$I\alpha = I/ab$$

$$Wb \alpha I \cdot abc$$

$$W \alpha I.$$

Therefore, the ratio between scattered light from particles and scattered light from the sample fluid is $$W/Wb \alpha I/abc.$$

Hence, when the S/N ratio of the signals from particles has been made constant, the particle acquisition ratio can be raised by making the product of the parameters bc larger and the parameter a smaller.

FIGS. 6 and 7 show a particle detection area using an elliptical laser beam. With this type of configuration, the scattered light reaching the photoelectric detector can be limited to the scattered light coming from particles in the diamond-shaped shaded portion. At this time, the visual field E and the depth F of the particle detection area 35 will usually be longer in the depth direction, as shown in FIG. 7. If the elliptical beam arrangement shown in FIG. 6 is adopted, the effective sensitivity of the depth range can be set low because changes in the beam intensity in the depth direction are abrupt.

The shape and size of the detection area 35 are decided by the F-number, focal distance, magnifying power of the light receiving lens 25, the width of the slit 26a and the like. In this invention, the direction A in which the particle travels is made to coincide with the depth F direction, in addition to which, as the laser beam is elliptical in shape, the intensity of the light received by the particles can be limited to within the full width at half maximum range E, enabling the detection accuracy to be further increased.

The measurement of fine particles in ultrapure water, using the above apparatus, will now be considered.

The size of particles present in ultrapure water is in the submicrometer range, and the concentration of the particles is low. Measurement of fine, sparsely-distributed particles such as these by means of the above light scattering method is an apt application inasmuch as individual particles can be detected. However, it is no easy task to measure individual submicrometer particles, because of the weakness of the scattering intensity. Therefore, a photomultiplier for counting photons is adopted as the photoelectric detector which receives, and converts to electrical signals, the weak scattered light.

When the above photomultiplier is used to receive weak scattered light of a constant intensity, it is known that the detection frequency of the output photoelectric pulse train will form a Poisson distribution, that is, when the number of pulses are counted at each of certain time intervals, the relationship between the count values and the frequency will form a Poisson distribution. Therefore, in the case, such as here, when particles in ultrapure water are to be measured, when the weak scattered light coming from passing particles is being extracted from among scattered light of a constant intensity from the water in the particle detection area, i.e., the background light, the photoelectric signal pulses thus obtained will include particle information in pulse trains which fluctuate in accordance with a Poisson distribution, and it becomes necessary to separate the changes in the scattering intensity accompanying the passage of a particle from the background light fluctuation.

Using an apparatus satisfying the above conditions, a system for recognizing fine particles in pure water was constructed.

FIG. 8 shows an example of the measurement of standard particles of 0.091 micrometers suspended in pure water, using the said measuring apparatus. In the figure, A is the pulse train as received from the photoelectric detector 27; the said background light shows a strong fluctuation that buries the signals related to particles. However, if the time series data of the pulses are subjected to the moving average process, the background light fluctuation is suppressed, as shown in B, enabling the particle signals to be extracted.

Thus, the recognition process sequence with respect to the time series data of the pulses corresponding to the scattering intensity, as acquired by the particle recognition system, is as follows.

1. Sampling of the time series data
2. Moving average processing
3. Analysis of smoothed time series data FIG. 9 shows an example of the embodiment of this particle recognition system. Data relating to the scattering of laser light accompanying the passage of particles obtained from the photoelectric detector 27 is sampled by the sampling unit 41 and written to a time series memory unit 43 by a time series data writing unit 42. At least two such memory units are provided (43 and 43'). On the basis of control by the CPU unit 40, time series data sent from the time series data writing unit 42 is written to one of the two memory unit, that is, the memory unit 43. When the memory unit 43 becomes full, the CPU unit 40 switches memory unit for the data to be written to memory unit 43'. At this stage the CPU unit 40 processes the data stored in memory 43, as explained later.

A ROM program memory and RAM working memory 44 is connected to the CPU unit 40. The CPU unit 40 also includes a comparator 40a for comparing the value of the moving average processed data with a predetermined value (L2) to determine whether the former value is larger than the latter, and a comparator 40b for comparing the time width that produces a scattering intensity exceeding the said predetermined value with the time of the passage of a particle through the particle detection area.

Connected to the CPU unit 40 is a parallel interface 45, and further connected thereto, via a printer interface 46 and an LDD driver 47 respectively, are a printer 48 and a 7-segment LED display 49 to form a configuration which enables the results of the measurements to be output to the display 49 and the printer 48.

FIG. 10 shows the method of the moving average processing of the time-series data. If M is the total number of sampled data in the one memory unit 43, the value of each data is $C_1$- $C_M$ and the moving average number is k, the nth of a time series data that has been subjected to moving average processing is $$C_n = \frac{1}{k} \sum_{i=1}^{k} C_{n+i-1}$$

This data is stored in the same memory location at which the data prior to processing was held. Thus, after the moving average of the nth data 43a has been calculated, it is written into the same nth memory location. This allows the memory space to be used economically.

Figure 11:
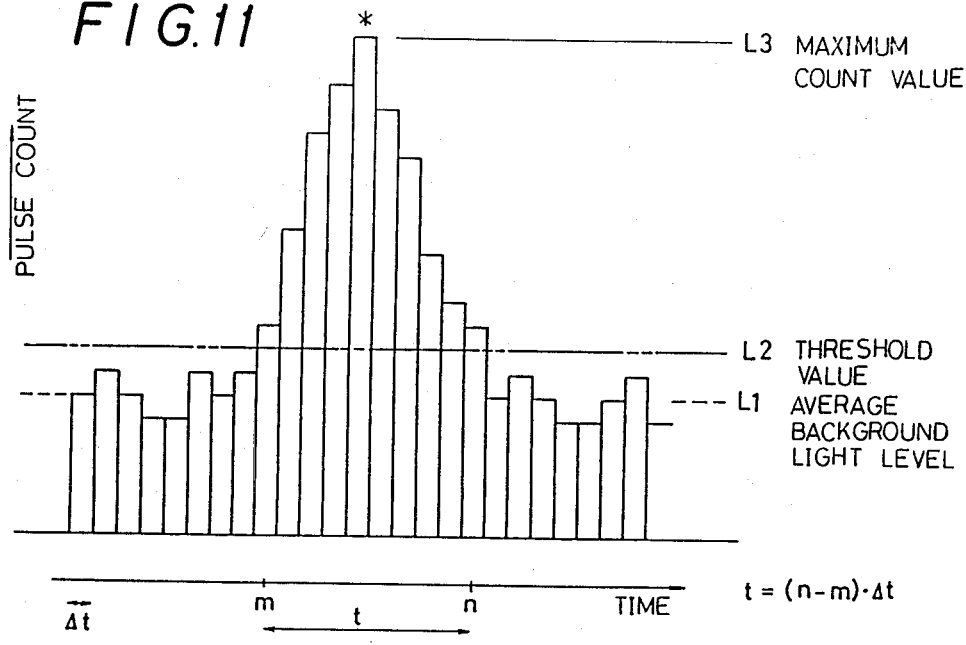
FIG. 11 is a explanatory view illustrating the particle recognition method.

Changes in count values corresponding to the passage of fine particles in the ultrapure water are extracted with respect to M−k+1 data processed as described above. This procedure will now be explained with reference to FIG. 11. In the figure the horizontal axis is the time base, corresponding to the data numbers in memory. The vertical axis shows the moving-averaged pulse count value for each sampling period Δt (corresponding to FIG. 8B). The count value level indicated as L1 is the average background level, and at a level exceeding that level is set a threshold value level L2. Particle recognition starts from when data that exceeds the threshold value is encountered in the course of comparison of the time series data being retrieved with the threshold value. When a continuous run of data that exceeds the threshold value continues to appear, the counts are compared while a maximum count value L3 is set. When the maximum count value is reached, each of the count values starts to decrease and the threshold value L2 is reached. At the stage where the count value becomes smaller than the threshold value, the number of data having a value that exceeds the threshold value is computed. In the figure, for example, the nth to rth data exceed the threshold value, so the interval D of the change in the count value that satisfies the condition particle recognition will be (n−m). The time width therefore is (n−m)Δt.

By comparing this time width with the time width tp of the particle's passage across the depthwise diameter of the elliptical beam that forms the particle detection area, an extracted change in the count value can be recognized as a change in the count value of the scattering intensity due to the passage of a particle. For accurate recognition performance, it is preferable that the time for the passage of the particle through the particle detection area is constant regardless of passage position or particle size. With regard to the position, as already explained, the width of the beam is limited to full width at half maximum by the mask 26 provided on the scattered light receiving side and, furthermore, because an elliptical beam is used so as to make intensity changes in the passage direction abrupt, no large change will be produced, but when the particle diameter changes from 0.07 to 0.2 micrometers, for example, the change in the interval of the count value based on differences in diameter will be large.

Because of this, the determination criterion is set as follows.

$$0.5 < (n-m)\Delta t/tp < 2$$

Preferably, the sampling period is set at about one-tenth the time width of the particle's passage through the particle detection area.

Figure 12:
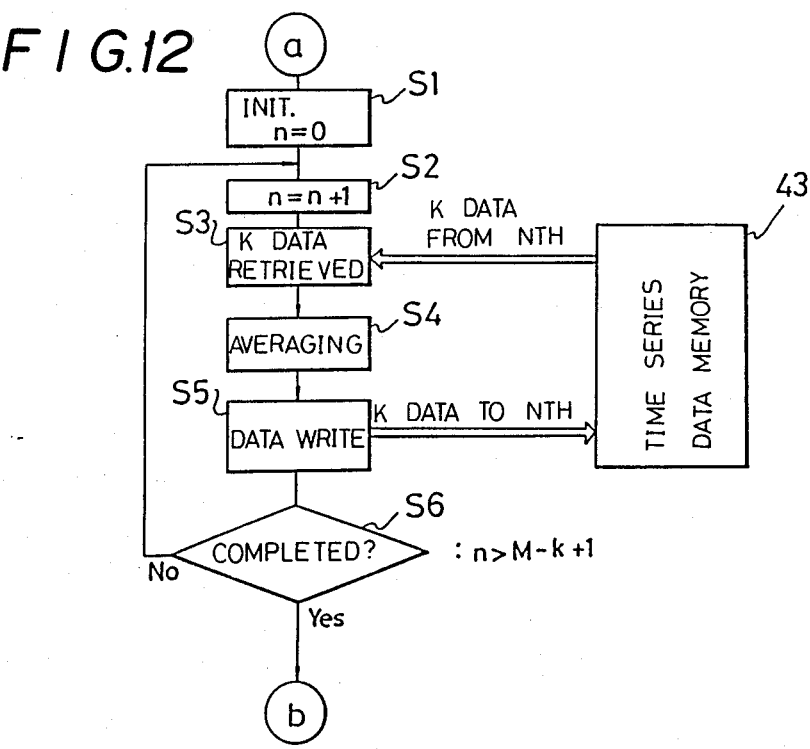
FIG. 12 is a flow-chart of the moving average processing of time-series data.
Figure 13:
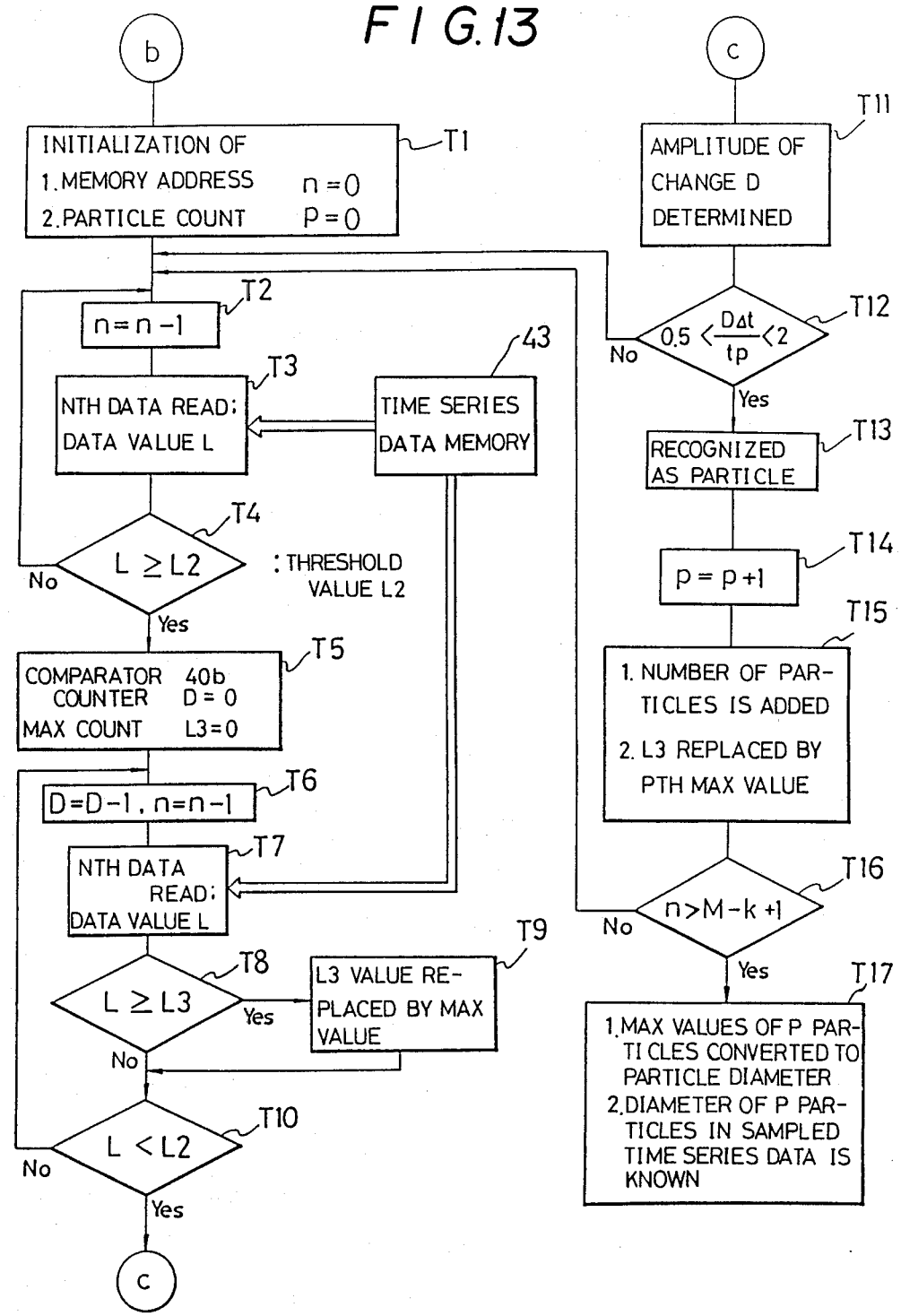
FIG. 13 is a flow-chart of the particle recognition algorithm.

FIGS. 12 and 13 show the algorithms for the moving average processing of the time series data and the particle recognition.

With reference to FIG. 12, sampling is performed in steps S1 to S6 until the processing of M−k+1 data has been completed. In step S3, k data are transferred from the nth data in the memory 43, the averaging operation is performed in step S4, and the result is written back to the nth data position of memory 43.

With reference to FIG. 13, in step T1 values are initialized, in steps T2 to T4 the nth data are sequentially read from memory 43 and compared with threshold value L2 by the comparator 40a, and data that exceed L2 are counted in steps T5 to T7 by the counter of comparator 40b. When a value exceeds the maximum count value L3, that value is substituted for value L3 in the maximum count value memory (steps T8 and T9).

In step T10, when the data value L has become smaller than L2, the interval D of the change is obtained in step T11, and if D is found to be within the predetermined interval (step T1), it is recognized as a particle and the particle is counted (steps T13 to T15). In step 116, if n has become larger than M−k+1, in step T17 the maximum count value of P particles is converted to particle size, obtaining the particle size of P particles from among the sampled time series data.

When employing the above criteria, it is necessary that the count values corresponding to the scattering intensity of the background light be stable. However, with the photon counting photomultiplier employed in the photoelectric conversion circuit and counting circuit of this invention, pulses are digitally counted, therefore there is none of the drift that occurs with analog amplifiers, and hence no need for any calibration to adjust for such drift.

Thus, in accordance with this embodiment, when a time width during which a change in the intensity of the scattered laser light occurs in which the time-series electric signal obtained corresponding to the scattered light exceeds a predetermined level, and when the said time width falls within a certain range, the change in the intensity of the scattered light is recognized as a change in intensity produced by the passage of a particle, enabling the accuracy of the measurement to be improved.

Especially when individual particles are being recognized, because the maximum count values of just the recognized particle count data are converted to particle size, providing the particle size and number distribution, high-resolution particle size measurement can be carried out.

Figure 14:
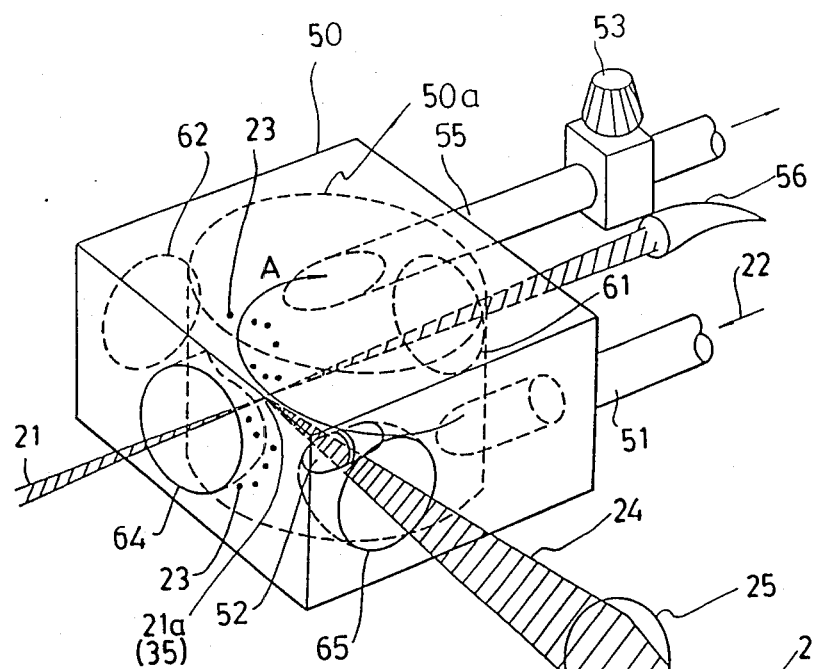
FIG. 14 is a structural view of another embodiment of a measuring apparatus according to this invention.

In the aforementioned embodiment the sample fluid is discharged after only one passage through the detection area. An example of a measuring cell to improve this transient use of the fluid is shown in FIGS. 14 to 16, comprising the mixing of a fluid flowing into the measuring cell with the fluid within the measuring cell to form a turbulent flow and using the inertia of the inflowing fluid or a stirrer or the like to form a stable whirling stream in the cell.

In each of the figures, the symbol 50 denotes a measuring cell inside which is formed a cylindrical portion 50a suitably shaped for the formation of the whirling stream and maintaining a more or less constant speed across the particle detection area 35. Affixed to the cylindrical portion 50a are a fluid intake tube 51 for feeding the sample fluid 22 containing particles 23 into the cylindrical portion 50a, and a fluid discharge tube 51 for discharging the fluid from the cylindrical portion 50a at a rate which is set by a regulator 53. Disposed on the floor of the cylindrical portion 50a is a stirrer 52 comprised of a magnet, for example, magnetically driven from the outside. As explained later, the stirrer 52 serves to promote the whirling action of the fluid mixed to make a turbulent flow, to form a whirling stream which traverses the particle detection area.

Figure 15:
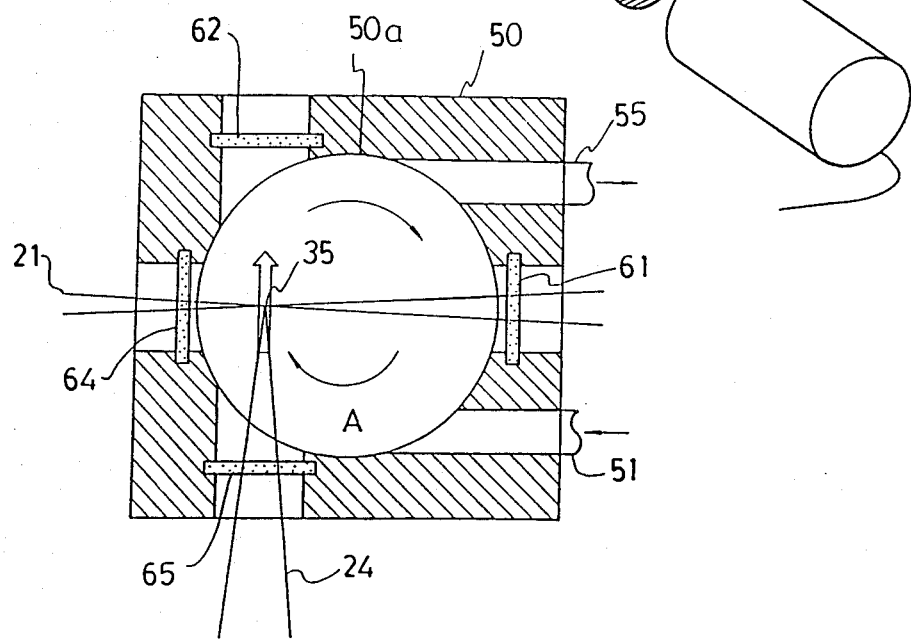
FIG. 15 is a sectional view of the principal parts of the apparatus of FIG. 14.
Figure 16:
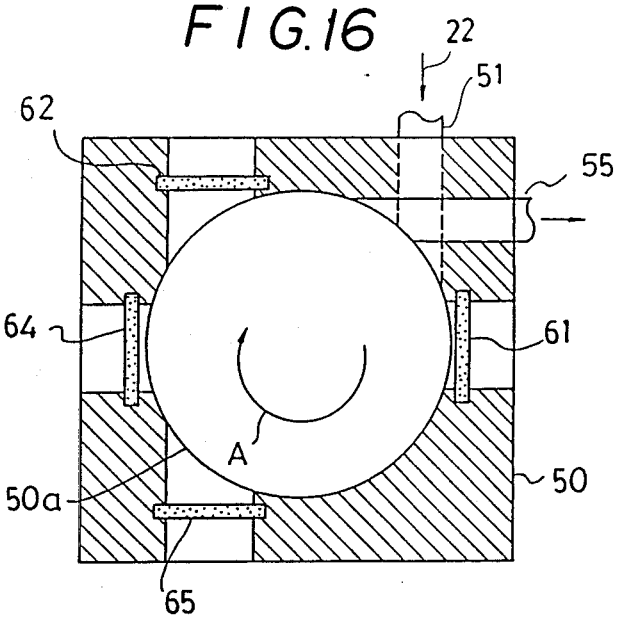
FIG. 16 is a sectional view of another embodiment of the measuring apparatus of this invention corresponding to the view shown in FIG. 15.

Arranged around the periphery of the cylindrical portion 50a of the measuring cell 50 are a beam entry window 64 through which the laser beam 21 from a laser light source (not shown) is projected, a beam exit window 61 through which the laser beam 21 exits, and a light receiving window 65 which receives the scattered light 24 from particles 23 passing through the laser beam focus point 21a (see also FIG. 15). A transparent window 62 for preventing reflection from the cell wall is provided at a position opposite the light receiving window 65 and the measuring area 21a. Each of the windows is formed of silica glass coated on both sides to impart low reflectance characteristics thereto with respect to the wavelength of the incident light. In addition, provided to the rear of the beam exit window 61 is a light trap 56 which absorbs the laser beam.

Disposed backward of the light receiving window 65 are the focussing lens 25, the mask 26, the photoelectric detector 27 for receiving scattered light 24 and converting it to electrical signals, and the processing apparatus shown in FIG. 9 is connected further back.

With this configuration, the sample fluid 22 flows into the cylindrical portion 50a in the measuring cell 50, via the fluid intake tube 51. As described later, the fluid flowing in and the fluid that is inside the cell mix at the junction of the fluid intake tube and the cylindrical portion to form a turbulent flow. The inflowing fluid passes through the detection area 35 and a portion thereof is discharged via the discharge tube 55, the amount discharged being only that set by the regulator 53. The spinning of the stirrer 52 at a constant speed stabilizes the circulation of the mixed fluid to form a whirling stream which passes through the detection area 35.

The laser beam 21 is projected in via the beam entry window 64 so that it focuses at the detection area 35. Scattered light 24 from particles 23 in the fluid passing through the focus point (35) of the laser beam 21 from the light receiving window 65 is formed into an image on the mask 26 by the lens 25, converted to electrical signals by the photoelectric detector 27 and subjected to the processing illustrated in FIGS. 9 to 13. The mask 26 is provided to limit the size of the measuring portion in the beam which detects the passage of particles. The laser beam 21 once focused diffuses as it exits the measuring cell 50 via the exit window 61 and is absorbed by the light trap 56.

With the method and apparatus for measuring particles in a fluid according to this embodiment, a mixing of the fluid is produced where the fluid intake tube joins the cylindrical portion in the measuring cell, and the mixture is formed into a stabilized whirling stream by the rotation of the stirrer provided in the measuring cell. The whirling stream formation conditions will now be considered. First, without taking into consideration the mixing of the fluids, the movement of the molecules in the fluid will cause particles 23 contained in the fluid to perform a Brownian motion. It is known that the average distance L a particle moves in time t as a result of Brownian motion, with a diffusion coefficient D, is $$L = \sqrt{6Dt}, D = kT/3\pi\eta d.$$

Here, k is a Boltzmann constant, T is the temperature of the fluid, $\eta$ is the coefficient of viscosity of the fluid, d is the particle diameter and $\pi$ is the ratio of the circumference of a circle to its diameter.

In the detection area 35, if the said time t is the time needed for one circuit as calculated from the peripheral speed produced by the whirling stream, then a particle that has passed once through the particle detection area will have deviated from the detection area by only a distance L one circuit later. Therefore, if the average distance L that the particle moves is made larger than the size of the measuring area 26a limited by the mask 26 shown in FIG. 14, that is, if it is set to slow the speed of the flow so that in the space of one circuit the particle is to be sufficiently displaced, a particle that passes once through the detection area can be regarded as not returning a second time to the area, even if only the effect of the Brownian motion is considered.

A state of turbulence is desirable at the connecting tube portion so that the fluid is sufficiently mixed. For this, the inside diameter of the connecting tube (the fluid intake tube) and the flow velocity $V_1$ in the tube are set so as to have a critical Reynold's number of at least $1.16 \times 10^3$. At the junction of the connecting tube and the cylindrical portion, the fluid spreads into a jet and mixes with the fluid in the cylindrical portion. If the change in the sectional area of the connecting tube and the cross-section formed by the height and radius of the cylindrical portion is increased, the cylindrical portion flow velocity $V_2$ can be reduced such as to $V_1 >> V_2$, and the Reynold's number for this portion can be set smaller than the critical Reynold's number. If in addition the whirling stream flow velocity $V_3$ induced by the rotation of the stirrer is made to satisfy the relationship $V_1 > V_3 > V_2$, the flow velocity in the cylindrical cell can be controlled by the speed of rotation of the stirrer. This presents the measurement of particle-scattered light from being affected by changes in the flow velocity $V_1$ in the connecting tube.

Under these conditions, the fluid in the measuring cell is spun at an appropriate rate by the rotation of the stirrer and fresh fluid flowing in through the fluid intake tube is being continually mixed in, so that particles in the fresh fluid are detected as the fresh portion of the fluid passes through the measuring area and the particle size and concentration distributions plotted against measurement time therefore accurately reflect the size and concentration distributions of the particles in the whole of the fluid.

In addition to the fluid intake tube and discharge tube configuration shown in FIGS. 14 and 15 whereby the above whirling stream is formed, i.e. a stable laminar flow is obtained in the particle detection area while at the same time the fluid is being mixed at the junction portion of the connecting tube, a configuration such as the one in the embodiment shown in FIG. 16 may also be used. In this embodiment the fluid intake tube 51 is disposed at right-angles to the discharge tube 55.

Whereas in the construction shown in FIG. 15 the fluid entering from the fluid intake tube reaches the detection area 35 after one quarter of a circuit, with the construction shown in FIG. 16 it takes a half circuit, which allows the mixed flow to become more stable. Also, in the embodiment of FIG. 16, the fluid discharge tube 55 is affixed directly above the intake tube 51, so that entrained air bubbles are discharged more rapidly and cannot easily remain in the cell. In FIGS. 15 and 16 the symbol A indicates the direction of the whirling stream.

With regard to the above embodiments, the invention has been explained from the aspect of the method of obtaining the particle size by analyzing the intensity of scattered light from the particles and the particle concentration from the number of passing particles and the amount of the fluid flow. However, this invention can also be applied to the method of obtaining particle diameter and its molecular weight based on the photon correlation method.

The apparatus according to the present invention can be utilized, for example, in the measurement of scattered light from particles in ultrapure water and the measurement of polymer particles present in paints and pigments.

Regarding each embodiment, when the optical axis has been adjusted to the optimum position, the particle detection area 35 defined by the slit 26a will be within the range shown by the shaded portion in the FIGS. 2, 7, and the visual field width E will be positioned at the center of the elliptical beam 21.

However, when the positional relationship of the adjusted mask and laser beam is disturbed by some external force, there is a possibility that particles will be detected passing through the low intensity fringe of the beam, degrading he particle size resolving power of the system. Because of this, as shown in FIG. 17, an actuator 28 is provided to move the mask 26.

FIG. 18A shows an example of the mask and laser beam maintained in an optimum positional relationship, while FIG. 18B shows when the relationship has been disturbed by an external force. With respect to the latter case, the control system by means of which the actuator is driven to restore the correct positional relationship will now be explained Pulses output by the photoelectric detector 27 corresponding to scattered light per unit sampling time are counted by the sampling unit 41 as shown in FIG. 19, and the counts for each sampling, become time series data and are stored in the time series data memory 43 of a microcomputer (CPU) 40 via the time series data writing unit 42. When the photoelectric detector used is a photomultiplier for photon counting that is suited to detecting weak light, the stored data will contain fluctuations in accordance with the laws of probability with respect to the photon detection process. In order to obtain the average light intensity received by the mask 26, moving average processing is performed with respect to the data stored in the memory to make it the control data for drive circuit 70. A ROM program memory and a RAM working memory 44 is connected to the microcomputer 40.

Figure 20:
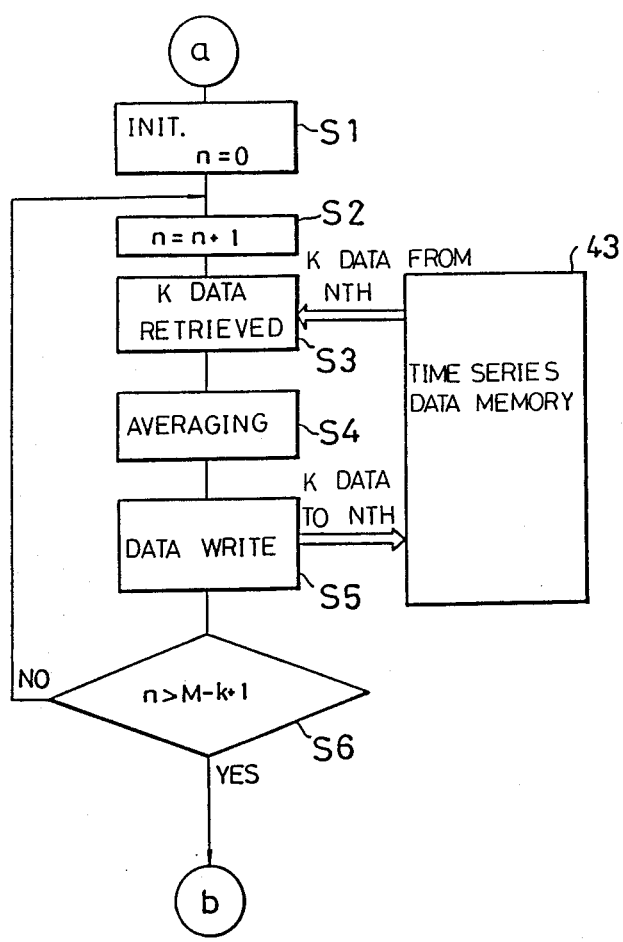
FIG. 20 is a flow-chart showing the moving average process for the time-series data.

The operation of the apparatus thus configured will now be explained with reference to the flowcharts of FIGS. 20 to 22.

Figure 17:
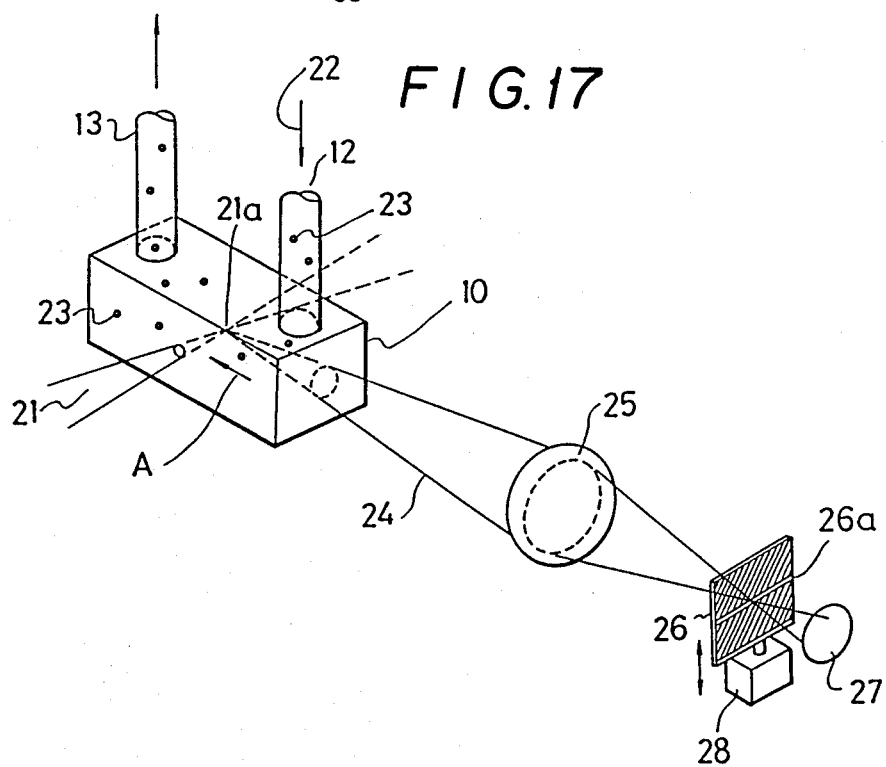
FIG. 17 is a perspective view of another embodiment of the apparatus of this invention
Figure 18:
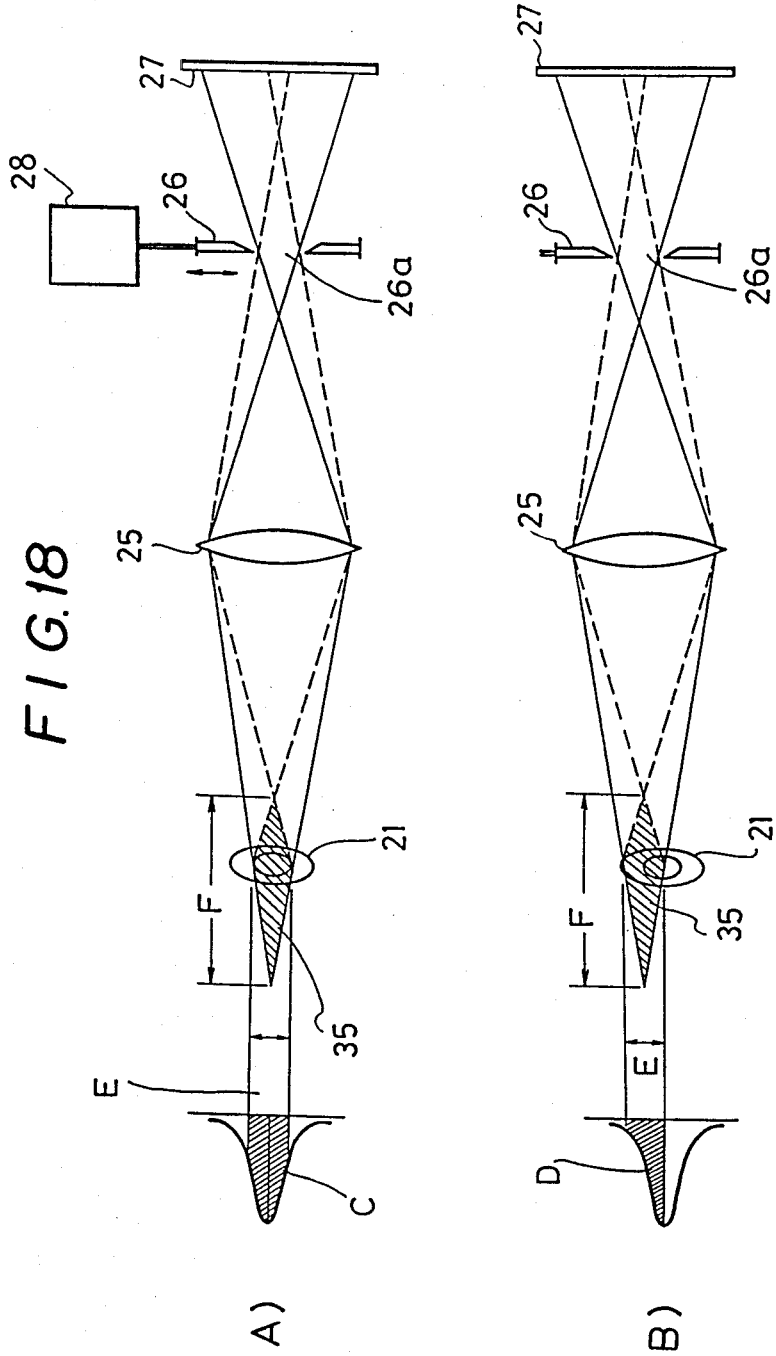
FIG. 18A is an explanatory diagram illustrating the optimum position of the mask in the measuring apparatus of FIG. 17.
FIG. 18B is an explanatory view showing the deviation from the optimum position.
Figure 19:
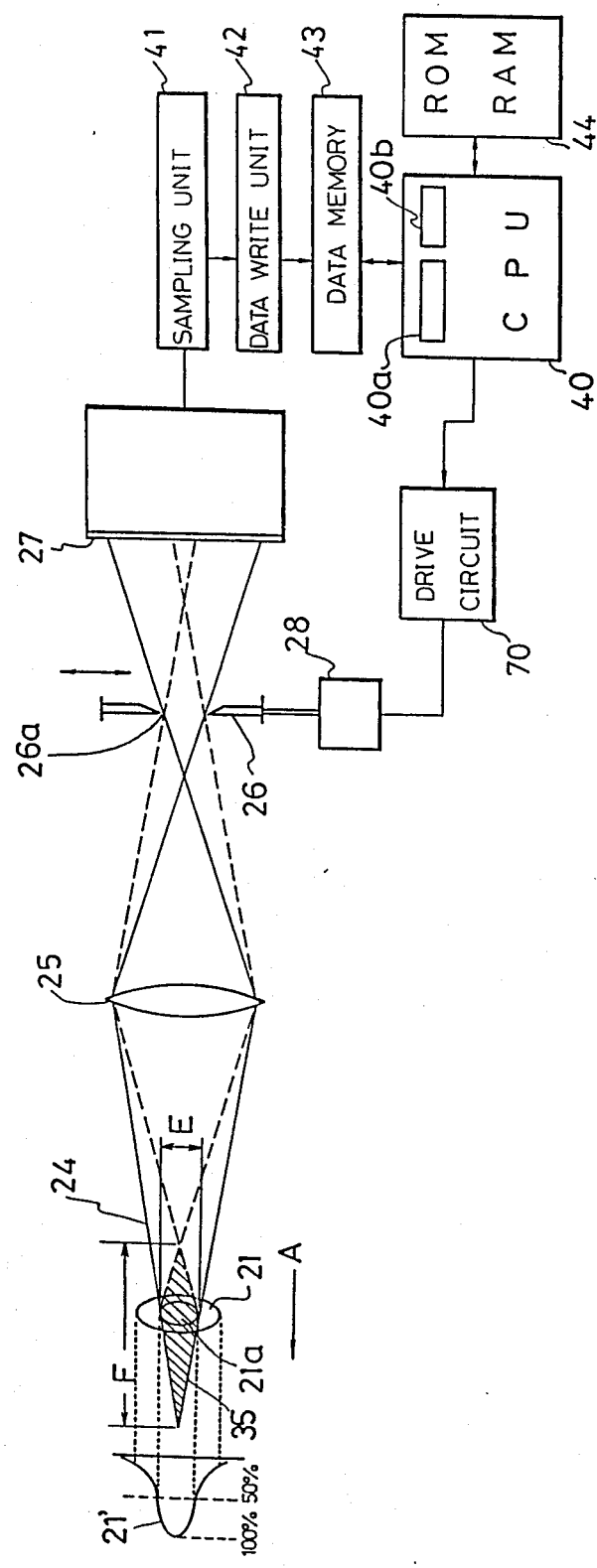
FIG. 19 is a structural view of the apparatus for moving the mask into the optimum position.

In FIG. 17, the elliptical laser beam 21 is focused to a spot 21a to form the detection area 35 shown in FIG. 18, and the sample fluid containing the particles 23 flows in direction A. Scattered light 24 produced by the laser light scattering from particles 23 is received by the photoelectric detector 27, via the light receiving lens 25 and the slit 26a. Pulses output from the photoelectric detector 27 corresponding to the scattered light are counted per unit sampling period by the sampling unit 41 and stored in the time series data memory 43, as has been described. At this time, moving average processing is performed to find the average intensity of the light received by the mask 26; the method used is shown in FIG. 20. In steps S1 to S3, memory address n is incremented and k data are transferred from memory 43, starting from the nth data. These data are averaged. The data thus averaged are returned to the nth data location in memory 43. If M is the total number of data, this is repeated until $n > M - K + 1$ (step S6), wherein the moving average processing for the time series data is carried out.

During this particle measurement, even if the axis of the incident laser beam 21 and the center of the slit 26a are both adjusted to a position where they intersect the axis of the light receiving lens 25, this alignment may be deviated by external forces, such as temperature changes, heat from the light source, vibration and the like. When this happens, as shown in FIG. 18B, the visual field width E limited b the slit 26 will go out of alignment with the center of the laser beam and the particle detection area will change to portion D, so that the part of the laser beam used will be the lower intensity portion. The result is that the intensity of light scattered from a particle will be decreased, and the detected particle will be recognized as a small particle. Also, the detection limit particle size will be increased with the detection capability reduced.

Here, with regard to the scattered light from the detection area used to detect the deviation, the continuous component is used that the scattered light from the particle detection area is proportional to the volume of the particle detection area. Because the scattered light from the particles passing through the detection area form strong signal pulses, it is not suitable for use as the deviation detection signal. However, because of the sparsity of the particles, such as in the case of the measurement of particles in ultrapure water, the average count values of the time series data which also include particle-scattered light may be used as control data.

In having the actuator 28 move the mask 26, the background light intensity at the mask position and the position itself are stored in memory, and the mask position at which the background light intensity is largest is found and the mask is moved to that position. By conducting this automatic mask position adjustment operation at set intervals, the detection area 35 limited by the mask slit position can be maintained in constant alignment with the center of the laser beam. This will enable particle size resolving power and particle detection capability to be maintained at a constant level.

Figure 21:
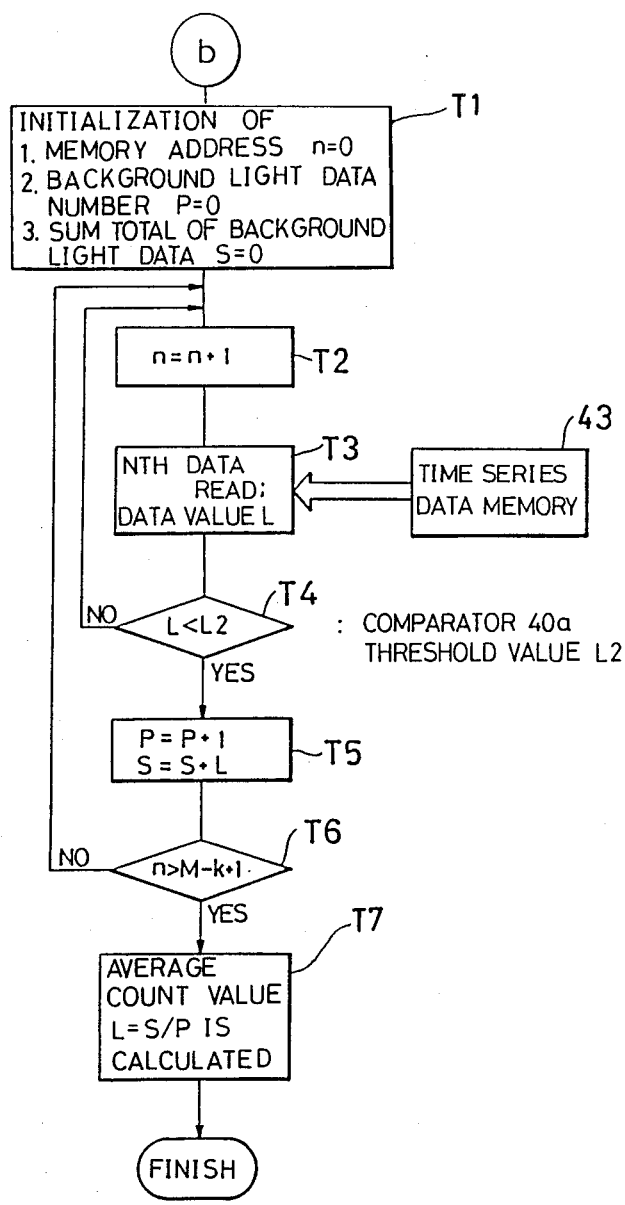
FIG. 21 is a flow-chart of the process of extracting the background light data.
Figure 22:
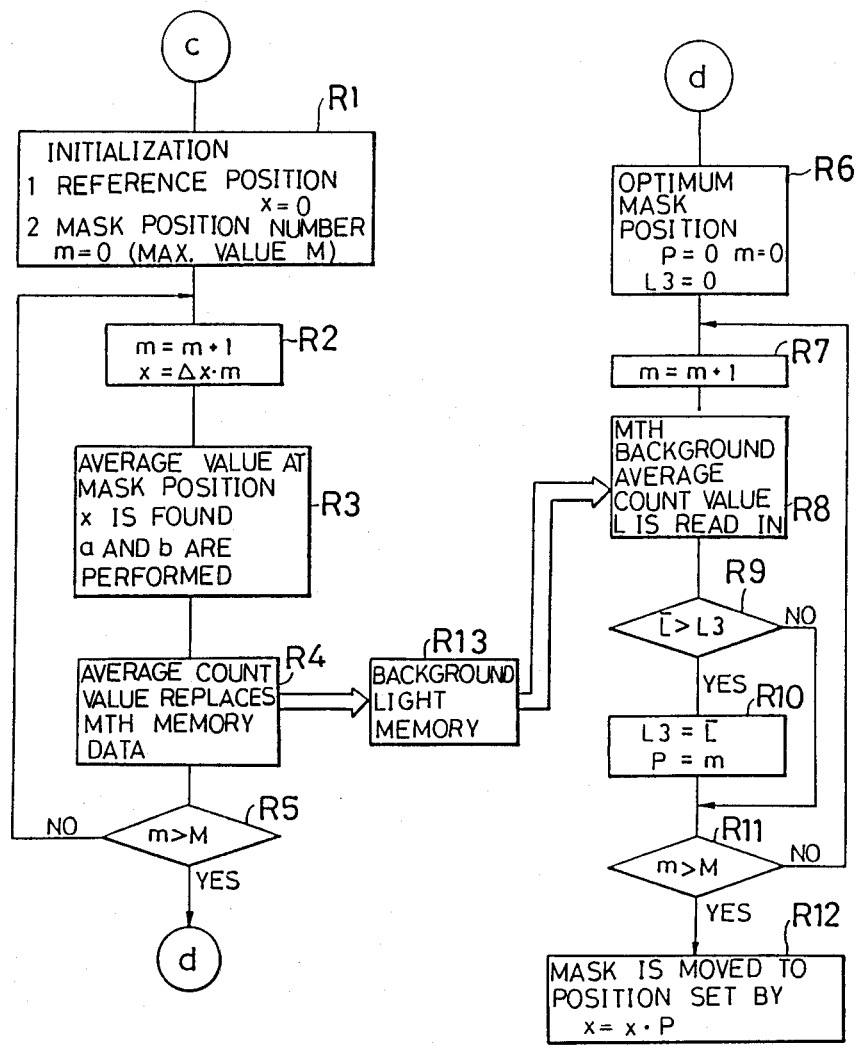
FIG. 22 is a flow-chart of the algorithm for automatically correcting the mask position.

The control sequence for realizing this method is shown in FIGS. 21 and 22.

First, background light data are extracted by the method shown in FIG. 21. In step T1 the various values are initialized. In steps T2 and T3 n is incremented, and the data at address n of memory 43 is read and taken as L. In step T4 this data value L is compared with threshold value L2 in the comparator 40a of the microcomputer 40 to extract the background light. Data smaller than L2 are regarded as background light. In step T5 the number of background light data P and the sum total S of the background light data values are obtained. This is repeated until n>M−k+1 (step T6). In step T7 the average $\overline{L}$=S/P of the counted values is obtained.

Next comes the automatic adjustment of the mask on the basis of the algorithm shown in FIG. 22.

In step R1 the mask 26 reference position x is initialized (x=0). The mask 26 position number m (maximum value of M) is initialized (m=0). Next, in step R2, the actuator 28 is driven by drive circuit 70 to move the mask. If the mask movement step is Δx, mask position x will become x =Δx. m. In step R3, the average count value of the background light at mask position x is obtained via the process shown in FIGS. 20 and 21, so that $\overline{L}$=S/P is obtained, and this value is stored in the mth memory in steps R4 and R13. This process is repeated until the mask position reaches the maximum value M (step R5).

When the mask position exceeds the maximum value M the mask is moved to d and controlled to reach the optimum position P. In step R6, optimum position P, mask position number m and constant L3 are each zeroed. In step R7 the mask position m is incremented and in step R8 the mth background light average count value $\overline{L}$ is read, via the background light memory. Then, in step R9, $\overline{L}$ is compared with L3. If it is larger than L3, the position is determined as being the optimum, and in step R10, values are taken as L3=$\overline{L}$, P=m, if $\overline{L}$ is smaller than L3 the process moves to step R11, and the above procedure is repeated until the mask position reaches maximum value M. When the mask position has reached the maximum value, the actuator 28 is operated in step R12 to move the mask to a position set by x=Δx. P. At this position the intensity of the background light in the scattered light is at its maximum, and the adjusted state is as shown in FIG. 18A.

It is possible for the problematic deviation of the laser beam axis mentioned in the foregoing to occur in the depth direction indicated in FIG. 18 by F or along the axis of the laser beam (normal to the sheet), but because of the large spread in the depth direction as set by the slit and the fact that the change in the diameter of the beam in the vicinity of the focus point is not abrupt, it can be handled with some latitude, compared with deviation in the visual field direction.

In the foregoing embodiment, the actuator 28 need not be attached to the mask 26, and can achieve its object by being provided on the receiving lens 25, the optical irradiation system or the light source. In such a case, the actuator may be provided so that it moves in a direction perpendicular to the direction of the mask slit on the imaging plane of the scattered light receiving lens 25.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. A method for measuring a particle in a fluid by irradiating the fluid containing the particle with a laser beam and analyzing the laser light scattered by the particle to determine the characteristics of the particle, comprising the steps of:
    forming in said fluid a particle detection area in which said particle to be measured is caused to flow;
    projecting said laser beam into said particle detection area with its section elliptical in form in said particle detection area; and
    receiving the laser light scattered by said particle in a direction along which said particle flows, and analyzing the same to determine the characteristics of said particle.

2. A method as set forth in claim 1, wherein said particle is caused to flow through said particle detection area substantially perpendicularly to the direction of projection of said laser beam.

3. A method as set forth in claim 1, wherein said laser beam is projected so that its longer axis of the elliptical section lies perpendicularly to the direction of flow of said particle in said particle detection area.

4. An apparatus for measuring particles in a fluid by irradiating the fluid containing the particle with a laser beam and analyzing the laser light scattered by the particles to determine the characteristics of the particles, comprising:
    a measuring cell in which a sample liquid containing particles to be measured is received;
    means for generating a laser beam;
    means for projecting said laser beam into a selected area in said measuring cell in which said particles are to be measured with its section elliptical in form in said selected area;
    means for generating in said selected area a flow of particles which passes in a direction substantially perpendicular to the direction of said laser beam;
    a photoelectric detector disposed in the direction of said flow of particles for receiving the laser light scattered by the particles; and
    means for processing a signal derived from said photoelectric detector to determine the characteristics of said particles.

5. An apparatus as set forth in claim 4, wherein said means for generating a flow includes means for effecting a circular flow of particles in said selected area of said measuring cell.

6. An apparatus for measuring particles in a fluid by irradiating the fluid containing the particles with a laser beam and analysing the laser light scattered by the particles to determine the characteristics of the particles, comprising:
    a measuring cell in which a sample liquid containing particle to be measured is received;
    means for generating a laser beam;
    means for projecting said laser beam into a selected area in said measuring cell in which said particles are to be measured.
    means for generating in said selected area a flow of particles which passes in a direction substantially perpendicular to the direction of said laser beam;
    a photoelectric detector for receiving the laser light scattered by the particles;
    a mask with a slit disposed in the front of said photoelectric detector for limiting the scattered laser light impinging thereon;

an actuator for driving said mask in a direction perpendicular to the direction along which said slit extends;

means for processing a signal derived from said photoelectric detector to determine the characteristics of said particles;

means for storing the position of said mask and the intensity of background light in the scattered laser light at the position of said mask; and means for effecting the successive driving of said mask until the mask reaches a position in which said intensity of background light is at a maximum.

7. A method for measuring particles in a fluid by irradiating the fluid containing the particle with a laser beam and analyzing the laser light scattered by the particle to determine the characteristics of the particle, comprising the steps of:

forming in said fluid a particle detection area in which said particle to be measured is caused to flow;

projecting said laser beam into said particle detection area; and receiving the laser light scattered by said particle for photoelectric conversion into a time-series photoelectric signal;

determining a time width during which a change in intensity of the scattered laser light occurs in which said time-series photoelectric signal exceeds a predetermined level; and recognizing the change in intensity of the scattered light as a change in intensity caused by the passage of said particle through said particle detection area when said time width falls within a certain range, and processing the photoelectric signal to determine the characteristics of said particle.

8. A method as set forth in claim 7, wherein said time-series photoelectric signal is subjected to a moving average process before said time width is determined.

9. A method as set forth in claim 7, wherein said predetermined level is set so as to remove the background light from the scattered light.

10. A method as set forth in claim 7, wherein the recognition whether the time width falls within the certain level is conducted by comparing the time width with the time during which said particle passes through the particle detection area.

11. A method as set forth in claim 7, wherein an elliptical laser beam is used as said laser beam.

12. A method as set forth in claim 7, wherein said laser light scattered by said particle is received in a direction along which said particle passes.

13. A method as set forth in claim 7, wherein said particle is caused to flow in said particle detection area in the form of a laminar stream.

14. An apparatus for measuring particles in a fluid by irradiating the fluid containing the particle with a laser beam and analyzing the laser light scattered by the particle to determine the characteristics of the particle, comprising:

a measuring cell in which a sample liquid containing particles to be measured is received;

means for generating a laser beam;

means for projecting said laser beam into a selected area in said measuring cell in which said particles are to be measured;

means for generating in said selected area a flow of particles which passes in a direction substantially perpendicular to the direction of said laser beam;

a photoelectric detector for receiving the laser light scattered by the particle for photoelectric conversion into a time-series photoelectric signal;

storage means for storing said time-series signal from said photoelectric detector;

means for comparing said photoelectric signal stored in said storage means with a predetermined level to obtain a time width during which the photoelectric signal exceeds said predetermined level to cause a change in intensity of the scattered light; and means for processing said time-series photoelectric signal to determine the characteristics of said particle;

wherein said change in intensity of the scattered light is recognized as a change in intensity caused by the passage of said particle through said particle detection area when said time width falls within a certain range.

15. A method for measuring a particle in a fluid by irradiating the fluid containing the particle with a laser beam and analyzing the laser light scattered by the particle to determine the characteristics of the particle, comprising the steps of:

forming in said fluid a particle detection area in which said particle to be measured is caused to flow;

focussing a laser beam having a beam waist into the center of said particle detection area;

receiving laser light scattered by a particle passing through said particle detection area with a lens and imaging the scattered light on a rectangular aperture disposed at an imaging point of the center of said particle detection area along the optical axis of said lens; and providing one side of said rectangular aperture shorter than the radius of the beam waist of said focused laser beam such that the intensity of said laser beam within an optically conjugate region of said rectangular aperture is more than one half of the maximum intensity at the focus point of said laser beam.

16. A method as set forth in claim 15, wherein said laser beam is focused to an elliptical cross-section in said particle detection area, with the major axis of said elliptical cross-section perpendicular to the direction of flow of said particle.

17. A method as set forth in claim 15, further comprising driving said aperture by an actuator in a direction perpendicular to a plane determined by both optical axes of said laser beam focused in said particle detection area and said scattered laser light received by said lens until the aperture reaches a position in which the intensity of light impinging on the aperture due to the fluid within said particle detection area is at a maximum.

18. A method for measuring a particle in a fluid by irradiating the fluid containing the particle with a laser beam and analyzing the laser light scattered by the particle to determine the characteristics of the particle, comprising the steps of:

forming in said fluid a particle detection area in which said particle to be measured is caused to flow;

projecting a laser beam into said particle detection area;

receiving laser light scattered by said particle and converting said scattered light into a time series of photoelectric pulses by photon counting;

determining a time width during which a change in intensity of the scattered laser light occurs in which said time series of photoelectric signal exceeds a predetermined level;

recognizing the change in intensity of the scattered light as the passage of said particle through said particle detection area when said time width falls within a certain range; and processing the photoelectric pulses to determine the characteristics of said particle.

19. A method as set forth in claim 18, wherein said time-series photoelectric signal is subjected to a moving average process before said time width is determined.

20. A method as set forth in claim 18, wherein said predetermined level is selected to remove background light due to said fluid within said particle detection area from the scattered light.

21. A method as set forth in claim 18, wherein the step of recognizing whether the time width falls within the certain level comprises comparing the time width with the time during which said particle passes through the particle detection area.

22. A method as set forth in claim 18, wherein an elliptical laser beam is used as said laser beam.

23. A method as set forth in claim 18, wherein the step of receiving said laser light scattered by said particle comprises receiving the light through a rectangular aperture set on an imaging point of a receiving lens.

24. A method as set forth in claim 18, wherein said particle is caused to flow in said particle detection area in a laminar stream.

25. A method for measuring particles in a fluid by irradiating the fluid containing the particles with a laser beam and analyzing the laser light scattered by a particle to determine the size distribution of the particles, comprising the steps of:

forming a particle detection area at a middle point of a wall and the center of a measuring cell having a cylindrical flow region;

introducing a sample fluid at an inflow rate through an inlet pipe, having a smaller diameter than the radius and the height of said cylindrical flow region, into said cylindrical flow region tangentially along an interior wall of said measuring cell;

mixing said sample fluid with fluid within said flow region to distribute said sample fluid into elements over the cross-section of said cylindrical flow region;

forming a swirling stream of mixture around said center of said cylindrical flow region;

stabilizing said swirling stream as a laminar flow by a stirrer rotating at said center of said cylindrical flow region;

detecting the particles contained in said elements of said sample fluid passing through said particle detection area at a constant rate in a uniform direction; and discharging part of said mixture flowing in said cylindrical flow region from an outlet pipe connected tangentially with the flow region and at a flow rate equal to the sample inflow rate.

26. An apparatus for measuring particles in a fluid by irradiating the fluid containing the particle with a laser beam and analyzing the laser light scattered by the particle to determine the characteristics of the particle, comprising:

a measuring cell comprising a cylindrical vessel, an inlet pipe and an outlet pipe both having the same inner diameter which is smaller than the radius or the height of said cylindrical vessel and both connected tangentially with an interior wall of the vessel, and windows formed in said interior wall;

means for introducing a sample fluid into said measuring cell and means for discharging said sample fluid from said measuring cell;

means for stabilizing a flow in said cylindrical vessel in a swirling laminar stream, comprising a rotatable stirrer located at the center of said cylindrical vessel;

means for generating a laser beam;

means for focussing said laser beam through one of the windows into a selected area located at the middle point of said interior wall and the center of said cylindrical vessel in which said particles are to be measured;

means for receiving the laser light scattered by a particle passing through said selected area, comprising a lens for collecting said scattered light and a rectangular aperture set at an imaging point of said lens to define a particle detection area within the region of said focused laser beam at said selected area; and photoelectric detecting means for measuring the light power received from said aperture by photon counting.

27. An apparatus as set forth in claim 26; further comprising an actuator for driving said aperture in a direction perpendicular to a plane determined by both optical axes of said laser beam focused in said particle detection area and said collecting lens, and means for stopping the driving of said aperture when the aperture reaches a position in which the intensity of light impinging on said aperture due to said fluid is at a maximum.

28. An apparatus as set forth in claim 26; wherein said means for focussing said laser beam includes means for projecting the beam with an elliptical cross-section in said selected area.

29. An apparatus for measuring particles in a fluid by irradiating the fluid containing the particle with a laser beam and analyzing the laser light scattered by the particle to determine the characteristics of the particle, comprising:

a measuring cell in which a sample fluid containing particles to be measured is maintained;

means for generating a laser beam;

means for projecting said laser beam into a selected area in said measuring cell;

photoelectric detecting means for receiving the laser light scattered by the particle and for converting said laser light into time-series photoelectric pulses by photon counting;

storage means for storing values associated with said time-series pulses from said photoelectric detecting means;

means for comparing said stored values in said storage means with a predetermined level to obtain a time width during which the photoelectric pulse exceeds said predetermined level; and means for processing said time-series photoelectric signal to determine the characteristics of said particle, including means for determining that a change in intensity of the scattered light is caused by the passage of said particle through said selected area when said time width falls within a certain range.

* * * * *